(12) United States Patent
Børgesen

(10) Patent No.: US 7,118,548 B2
(45) Date of Patent: Oct. 10, 2006

(54) DEVICE FOR THE TREATMENT OF HYDROCEPHALUS

(75) Inventor: Svend Erik Børgesen, Kokkedal (DK)

(73) Assignee: Sinu Shunt A/S, Glostrup (DK)

( * ) Notice: Subject to any disclaimer, the term of this patent is extended or adjusted under 35 U.S.C. 154(b) by 488 days.

(21) Appl. No.: 09/858,951

(22) Filed: May 17, 2001

(65) Prior Publication Data

US 2002/0128588 A1 Sep. 12, 2002

Related U.S. Application Data

(63) Continuation of application No. 09/147,833, filed on Mar. 16, 1999.

(30) Foreign Application Priority Data

Sep. 18, 1996 (DK) .............................. 1022/96

(51) Int. Cl.
*A61M 5/00* (2006.01)

(52) U.S. Cl. .......................................................... 604/9
(58) Field of Classification Search ............... 604/8–10, 604/128, 129, 523
See application file for complete search history.

(56) References Cited

U.S. PATENT DOCUMENTS

| | | | |
|---|---|---|---|
| 3,233,610 A | 2/1966 | Wade et al. | 128/8 |
| 3,566,875 A | 3/1971 | Stoehr | 128/350 |
| 3,583,387 A | 6/1971 | Garner et al. | |
| 3,894,541 A | 7/1975 | El-Shafei | 128/350 |
| 4,182,343 A | 1/1980 | Inaba | 128/350 R |
| 4,377,169 A | 3/1983 | Banks | 604/8 |
| 4,382,445 A | 5/1983 | Sommers | |
| 4,438,773 A | 3/1984 | Letterio | |
| 4,500,311 A | 2/1985 | Redmond et al. | |
| 4,578,057 A | 3/1986 | Sussman | |

(Continued)

FOREIGN PATENT DOCUMENTS

| | | |
|---|---|---|
| DE | 198 20 808 | 11/1999 |
| EP | 066 685 | 12/1986 |
| EP | 344 895 | 12/1989 |
| EP | 0 363 873 | 4/1990 |
| EP | 409 511 | 1/1991 |
| EP | 0 982 048 A1 | 3/2000 |
| GB | 2 330 078 | 4/1999 |
| WO | 96/37144 | 11/1996 |
| WO | 98/11934 | 3/1998 |
| WO | 99/24097 | 5/1999 |
| WO | 99/30746 | 6/1999 |
| WO | 99/58053 | 11/1999 |

OTHER PUBLICATIONS

Michael J. Albeck, M.D., et al., "Age dependency of resistance to cerebrospinal fluid outflow," Journal of Neurosurgery, vol. 89, Aug. 1998, pp. 275–278.

(Continued)

*Primary Examiner*—Loan H. Thanh
(74) *Attorney, Agent, or Firm*—Browdy and Neimark, P.L.L.C.

(57) ABSTRACT

A cerebrospinal fluid shunt system comprises a brain ventricular catheter for insertion into the brain ventricle so as to drain cerebrospinal fluid from the brain ventricle. The system also comprises a sinus sagittalis catheter for insertion into the sinus sagittalis for feeding the cerebrospinal fluid into sinus sagittalis. A shunt main body is connected at one end thereof to the brain ventricle catheter and at another end thereof to the sinus sagittalis catheter. The shunt main body can provide fluidic communication between the brain ventricle catheter and the sinus sagittalis catheter. The system further comprises a tubular flow passage restricting member defined within the shunt main body. The tubular flow passage restricting member defines a resistance to flow of 8–12 mm Hg/ml/min.

31 Claims, 12 Drawing Sheets

U.S. PATENT DOCUMENTS

| | | | |
|---|---|---|---|
| 4,605,395 A | * 8/1986 | Rose et al. | 604/8 |
| 4,646,752 A | 3/1987 | Swann et al. | |
| 4,781,673 A | 11/1988 | Watanabe | 604/9 |
| 4,781,674 A | 11/1988 | Redmond et al. | 604/9 |
| 4,784,648 A | 11/1988 | Singh et al. | 604/141 |
| 4,903,707 A | 2/1990 | Knute et al. | |
| 4,904,236 A | 2/1990 | Redmond et al. | 604/9 |
| 5,000,731 A | * 3/1991 | Wong et al. | 604/8 |
| 5,042,974 A | 8/1991 | Argarwal | 604/9 |
| 5,054,497 A | 10/1991 | Kapp et al. | |
| 5,891,100 A | 4/1999 | Fleckenstein | |
| 6,283,934 B1 | 9/2001 | Børgesen | |

OTHER PUBLICATIONS

S.E. Bergesen et al., "Measurement of Resistance to CSF Outflow– Clinical Experiences in 333 Patients", Intracranial Pressure, VII, pp 353–355.

A. Aschoff et al., "Overdrainage and shunt technology", Child's Nerv Syst (1995) 11:193–202.

A. Aschoff et al., "The history of valved shunts. A review on 177 historical, recently available and prototype valves," XXV Annual Congress of Int'l Society of Pediatric Neurosurgeons, Verona 13–18$^{th}$, Sep. 1997.

A. Aschoff et al., "Overdrainage and shunt technology", Child's Nerv Syst (1995) 11:193–202.

C.J. Hash et al., "Ventricle to Sagittal Sinus Shunt for Hydrocephalus", Neurosurgery, vol. 4:5.

J.M Drake et al., The shunt book, p 146, 1985.

H.L. Wen, "Ventriculo—Superior Saggital Sinus Shunt for Hydrocephalus", Surgical Neurology, vol. 17, No. 6, pp 432–434, Jun. 1982.

S.E. Bergesen et al., "Measurement of Resistance to CSF Outflow– Clinical Experiences in 333 Patients", Intracranial Pressure VII, pp 353–355.

S.E. Bergesen et al., "Relationships between intracranial pressure, ventricular size, and resistance to CSF Outflow", J. Nerosurg 67:535–539, 1987.

S.E. Borgesen et al., "Measurement of Resistance to CSF Outflow by Subarachnoid Perfusion", Outflow of Cerbrospinal fluid, Alfred Benzon Symposium 27, pp. 121–129, 1989.

S.E. Borgesen et al., "The predictive value of conductance to outflow of CSF in normal pressure Hydrocephalus", Brain 105, pp. 65–86, 1982.

* cited by examiner

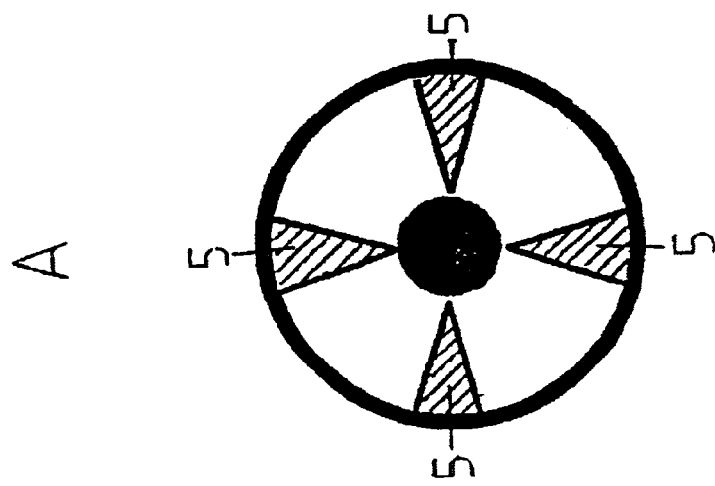
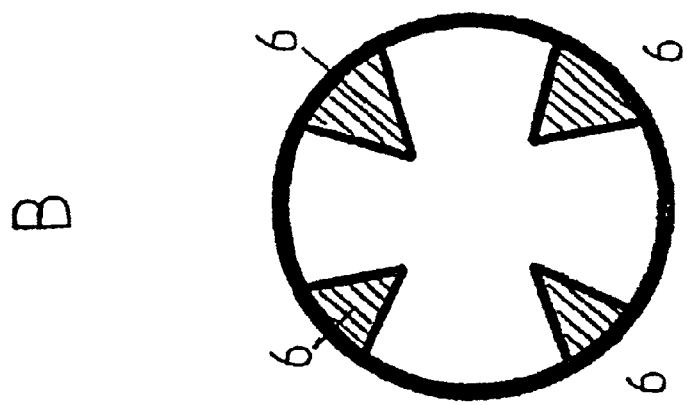
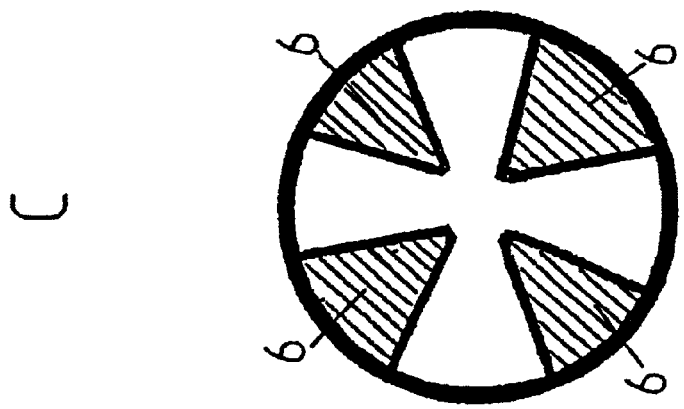
Fig. 4

DEVICE FOR THE TREATMENT OF HYDROCEPHALUS

This application is a continuation of U.S. Ser. No. 09/147,833, filed Mar. 16, 1999.

The present invention relates to a cerebrospinal fluid shunt system for shunting cerebrospinal fluid from the brain ventricles to sinus sagittalis.

GENERAL BACKGROUND

Cerebrospinal fluid is formed in the ventricular system irrespective of the intracranial pressure (ICP). The formation rate is constant, with a range of 0.3–0.4 ml/min. (Borgesen and Gjerris 1987). Hydrocephalus, i.e. a pathological increase in the amount of intracranially located cerebrospinal fluid, arise when the outflow of the cerebrospinal fluid is obstructed leading to an increase in the intracranial pressure and in the amount of intracranially located cerebrospinal fluid. The obstruction may be localized in the aqueduct or the IV ventricle or in the normal resorption sites in villi arachnoidales in connection with the sagittal sinus. Pathoanatomically, hydrocephalus is divided in communicating or non-communicating hydrocephalus dependent whether there is passage between the ventricular system and sinus sagittalis or not. Communicating hydrocephalus, which is generally caused by obstruction located in the villi arachnoidales for example due to fibrosis formed in response to bleeding in the liquor, is the most common form of hydrocephalus.

The treatment of hydrocephalus aims at reducing the intracranial pressure to normal, physiological values and thereby also reducing the amount of cerebrospinal fluid towards normal, physiological values. This is obtained by deducting cerebrospinal fluid (CSF) from the ventricular system to another resorption site, bypassing the pathological obstruction by use of a CSF shunt. The most suitable diversion sites for CSF have been found to be the right atrium of the heart and the peritoneal cavity. Valves have been designed to hinder retrograde flow in the drainage system which could occur due to pressure differences between the intracranial cavity and the resorption site, e.g. in connection with increased chest and/or abdominal pressure in connection with e.g cough or defecation.

Until the last 6 years the CSF shunts have been based on the principle of maintaining a constant ICP regardless of the flow-rate of CSF. The CSF shunts have been constructed to cut off CSF-flow when the differential pressure between the inlet and the outlet of the CSF shunt was reduced to a predestined level, called the opening pressure of the shunt. This has been necessary in order to maintain a basal ICP due to the use of an unphysiological resorption sites located outside the intracranial cavity. Example of a such ICP shunt is shown in U.S. Pat. No. 4,904,236 which is a fluid flow control device for controlling the flow of fluid from one region of the body to be drained to another region.

Clinical experience has proven that this principle of shunting is not an ideal solution. Sudden rises of the ICP, e.g. due to change of position, physical exercise, or pathological pressure waves result in excessive CSF drainage. This so-called hyperdrainage leads to subnormal ICP for shorter or longer periods of time. Several reports in the literature (Aschoff et al., 1995) point at problems due to this hyperdrainage, and especially the pronounced narrowing of the ventricles has been pointed out to be the main factor leading to malfunctioning of the implanted shunting device. The reason is that the ventricular walls may collapse around the ventricular CSF shunt device, and particles (cells, debris) may intrude into the shunt device.

This has led to introduction of multiple designs of drains to be used in the ventricular cavity. An effect of these different drain designs on the complication rates of shunts has not been proven.

In the recent years CSF shunt devices have been introduced which aim at regulating the flow rate of CSF, see e.g. U.S. Pat. No. 4,781,673 which describes a brain ventricle shunt system with flowrate switching means.

An alternative flow regulating mechanism of the Orbis Sigma shunt results in partial closure of the shunt at increases in the differential pressure above 10 mm Hg, and in reopening of the shunt when the differential pressure exceeds 35 mm Hg. It has been shown that this type of shunt indeed leads to a reduction of the complication rate of the system. Another shunt system, The Pudenz Delta valve, also hinders excessive CSF outflow at higher pressure levels. U.S. Pat. No. 4,605,395 is an example of a shunt device comprising a nonlinear hydraulic filter valve which closes in the event of large changes in flow rate.

Still, the above CSF shunt systems drain the CSF to a resorption site that is far from normal and to a site where the pressure difference over the shunt may differ substantially from the normal, physiological pressure ranges.

Occasional reports in the literature have described the use of ventriculo-superior sagittal shunts for the treatment of hydrocephalus (Hash et al., 1979 and Wen, 1981). In the article by Hash et al. it is concluded that the described technique wherein a low-low or extra-low pressure one way valve is used may be suitable for patients with high pressure hydrocephalus and of particular value in very ill or debilitated patients because of the rapidity with which it can be performed under local analgesia whereas its use in normal or low pressure hydrocephalus must still be evaluated. This article is followed by a comment by the editor that there are a multitude of remaining critical questions. One of the problems not addressed in this study is overdrainage due to the fact that the used valve is not flow-restricting.

Wen reports the treatment of fifty-two children with hydrocephalus with ventriculo-superior sagittal sinus shunts by use of a modified Pudenz tube. In this tube there is provided slits which provide an opening pressure of about 6 mm Hg. No clear conclusion can be drawn from this report except that shunting to the sagittal sinus does not inherit serious complications.

EP 066 685 describes a drain comprising a bundle of one or more microtubules, each being about 0.44 mm in diameter for controlling hydrocephalus comprising a plurality of pliable microtubular members for conducting cerebrospinal fluid from the cerebral ventricle to selected areas of the human body, e.g. to the subarachnoid space. Essentially, this patent relates to a draining system aiming at avoiding obstruction due to clotting of the draining system and is not flow-regulating.

SUMMARY OF THE INVENTION

The device for treatment of hydrocephalus of the invention leads the CSF from the ventricles to the sagittal sinus beneath the sagittal suture. The present invention thus provides a CSF shunt system that treats the hydrocephalus by bypassing the pathological obstruction, but diverts the CSF into its normal resorption site, and the pressure difference over the CSF shunt system is similar to the physiological pressure differences between the ventricles and the resorption site, thus regulating the CSF flow to be within the normal range and avoiding complications due to hyper drainage. Where appropriate, the present invention also relates to a method of treating hydrocephalus by use of the cerebrospinal fluid shunt system of the invention.

LEGENDS TO FIGURES

FIG. 4 shows three cross-sections through the check valve with the ball of the check valve.

DETAILED DISCLOSURE OF THE INVENTION

Figure 1:
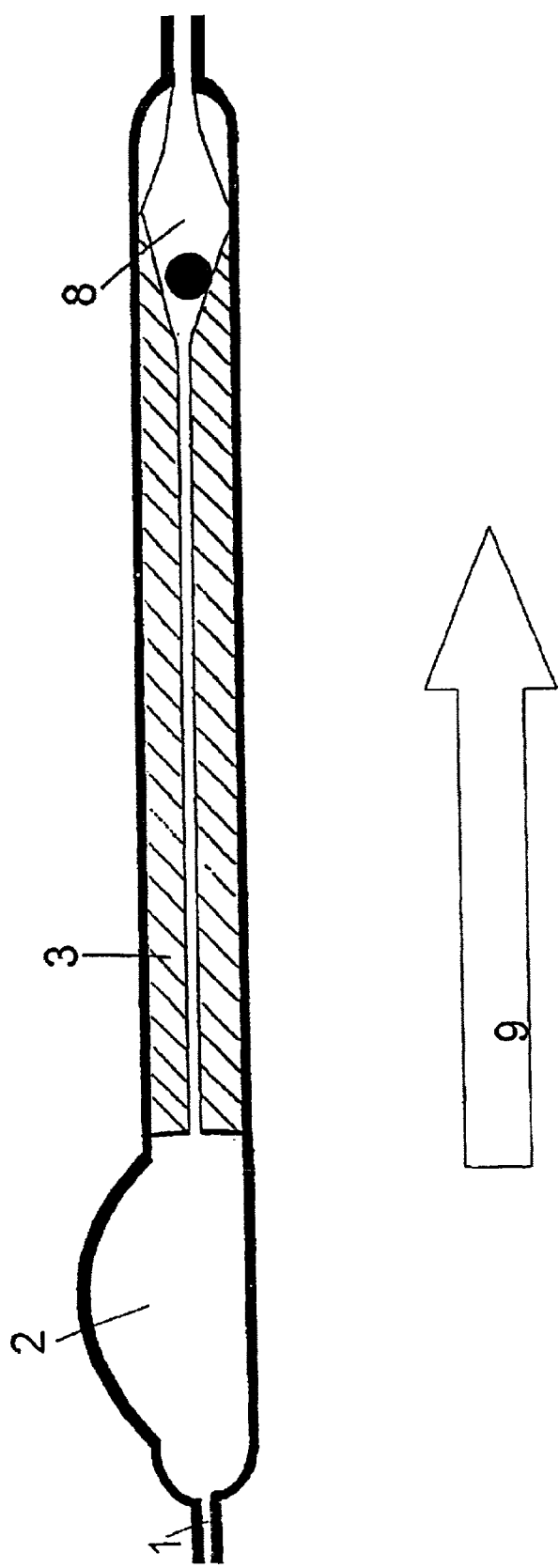
FIG. 1 shows a cerebrospinal fluid shunt according to an embodiment comprising an antechamber, a flow regulator, and a check valve connected in series.

In normal conditions the CSF is produced in the chorioid plexus in the ventricles. It flows through the ventricles, aqueduct and basal cisterns over the cerebral surface to the arachnoid villi, from where the CSF is absorbed into the sagittal sinus.

From measurements in 333 patients (Borgesen and Gjerris 1987) and 52 normal humans (Albeck, Borgesen et al. (submitted for publication)) it has been possible to establish the relationship between CSF production rate (FR), intracranial pressure (ICP), pressure in the sagittal sinus (Pss) and the resistance to outflow of CSF (Rout):

$$ICP = FR*Rout + P_{ss}$$

The relation between the intracranial pressure and the formation rate is linear, and the production rate measured was found to be 0.3 ml/min. (Borgesen and Gjerris 1989).

The detailed knowledge on CSF-dynamics, obtained in the laboratories at the Department of Neurosurgery, Rigshospitalet, Copenhagen, Denmark, has provided the necessary data which could make it possible to define a CSF shunt system that imitates the normal, physiological drainage of CSF. However, until the present invention, it has not been proposed or contemplated to use this knowledge to design a cerebrospinal fluid shunt system as outlined in the following.

The present invention relates to a cerebrospinal fluid shunt system comprising brain ventricle catheter means for insertion into the brain ventricle so as to drain cerebrospinal fluid from said brain ventricle; sinus sagittalis catheter means for insertion into the sinus sagittalis for feeding said cerebrospinal fluid into sinus sagittalis; shunt main body means connected at one end thereof to said brain ventricle catheter means and at another end thereof to said sinus sagittalis catheter means for providing fluidic communication between said brain ventricle catheter means and said sinus sagittalis catheter means; and tubular flow passage restricting means defined within said shunt main body and fluidically connecting said brain ventricle catheter means and said sinus sagittalis catheter means, said tubular flow passage restricting means defining a system total resistance to flow of 8–12 mm Hg/ml/min. Preferably, the resistance to flow is about 10 mm Hg/ml/min.

Essentially, the tubular flow passage restricting means for fluidically connecting the brain ventricle and the sinus sagittalis could in itself act as a brain ventricle catheter means and a sinus sagittalis catheter means thus making the construction very simple, the only limiting factor being that the device should define a resistance to flow of 8–12 mm Hg/ml/min.

Optionally, the cerebrospinal fluid shunt system further comprises check valve means disposed within said shunt main body for preventing said cerebrospinal fluid from flowing back from said sinus sagittalis catheter to said brain ventricle catheter.

By designing the shunt to exert a substantially constant resistance to outflow at the normal level, and by using the sagittal sinus as the resorption site, the drainage of CSF is regulated by the normal pressure differences between the production and the resorption sites. Excessive increases of the intracranial pressure are paralleled by increases also in the sagittal sinus, and the CSF outflow through the shunt is impeded by a resistance in the normal range. Hyperdrainage is then totally avoided.

The innovation is thus to use the recently defined levels of the normal resistance to CSF outflow and create a resistance to CSF-outflow in the shunt similar to the normal resistance. By using the sagittal sinus as the recipient site, physiological increases of the intracranial pressure will not increase the differential pressure over the shunt. Posture-related changes in the differential pressure as seen in shunts leading the CSF to the right atrium of the heart or to the peritoneal cavity are completely avoided. Overdrainage which is the most frequent reason for shunt failure in conventional shunts is thus also avoided.

Including a check valve such as a ball valve in the shunt will hinder any reflux of blood from the sagittal sinus into the shunt (or the ventricles). The check valve is constructed in such a way that it has substantially no resistance to the CSF flow through the shunt and has substantially no pressure threshold to be overcome for the intracranial pressure. The check valve which hinders retrograde flow of blood from the sagittal sinus can e.g. be constructed as a silicone ball of the same mass weight as CSF, which is placed in a chamber where the proximal, upstream inlet can be occluded by the ball, and where the distal, downstream end is kept open by ridges (6) around the orifice.

According to a preferred embodiment, the check valve comprises four guiding ridges (5) and four guiding and abutment ridges (6) in the chamber of the check valve. The ridges (5, 6) extend parallel to the direction of flow of the liquid. The guide ridges (5) extend from the inlet side of the chamber of the check valve till approximately the middle of the chamber of the check valve where the guide and abutment ridges (6) start and extend to the outlet side of the chamber. The ridges (6) serve to prevent the ball (4) of the check valve from reaching the outlet opening of the chamber of the check valve. The radial placing of the ridges (5, 6) can be directly recognized from FIG. 4.

The use of the sagittal sinus as a permanent reception site for CSF inherits a risk of complicating thrombosis of the sagittal sinus. Placing a permanent drain in the sagittal sinus has previously been used in attempts to treat hydrocephalus. A pressure regulating shunt system has been connected to a drain inserted in the sagittal sinus. The results have been reported in two papers, including in total 70 patients (Hash et al. 1979; Wen, 1981). Thrombosis of the sinus was not seen in any of the reported cases. Hydrocephalus could be treated by this method, but because of the use of a shunt type with in-built, predefined opening pressure the shunts were only effective in cases with very high intracranial pressure.

The flow of blood in the sagittal sinus has been measured at MRI studies. The very high flow in the range above 400 ml/minute probably hinder formation of thrombus around the drain or in the sinus. As a part of the present project, the effect of placing a drain in the sagittal sinus was analyzed in an animal investigation. In 5 dogs a silicone rubber catheter was placed in the sinus and observed for more than 3 weeks. Examination of the drain, the walls of the sinus, and the sinus itself did not macroscopically or at histological examination show any sign of thrombosis or endothelial proliferation on the drain or in the sinus.

In a preferred embodiment of the cerebrospinal fluid shunt system, the internal radius (R) of the tubular flow passage restricting means is less than about 0.20 mm and the flow-restricting part of the tubular flow passage restricting means has a length (L) which is calculated according to the law of Hagen-Poiseulle taking into consideration the aim to an provide a resistance to CSF-outflow through the shunt which is similar to the normal resistance, i.e. 8–12 mm Hg/ml/min such as about 10 mm Hg/ml/min. In particularly preferred embodiments, the internal radius (R) of the tubular flow passage restricting means is e.g. about 0.10 mm, about 0.11 mm, about 0.12 mm, about 0.13 mm, about 0.14 mm, about 0.15 mm, about 0.16 mm, about 0.17 mm, about 0.18 mm or about 0.19 mm and the length (L) is calculated accordingly.

Figure 10:
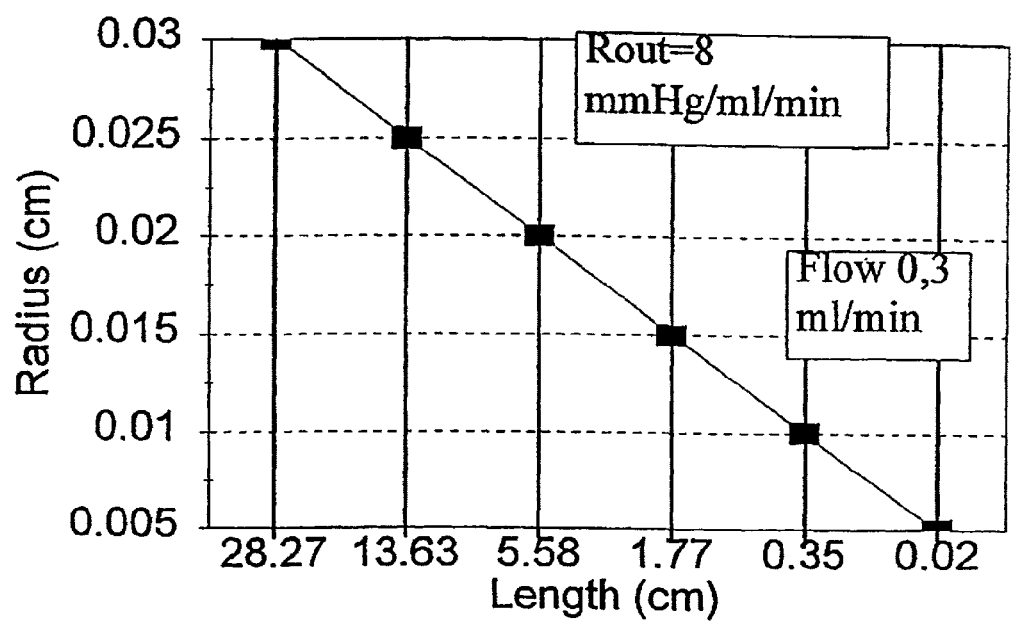
FIG. 10 shows the influence of the length on the radius given a resistance to outflow at A. 8 mm Hg/ml/min, B. 10 mm Hg/ml/min and C. 12 mm Hg/ml/min. In these particular examples, the differential pressure is 4 mm Hg and the viscosity is 0.0072 dyn*sec/cm$^2$.
Figure 10B:
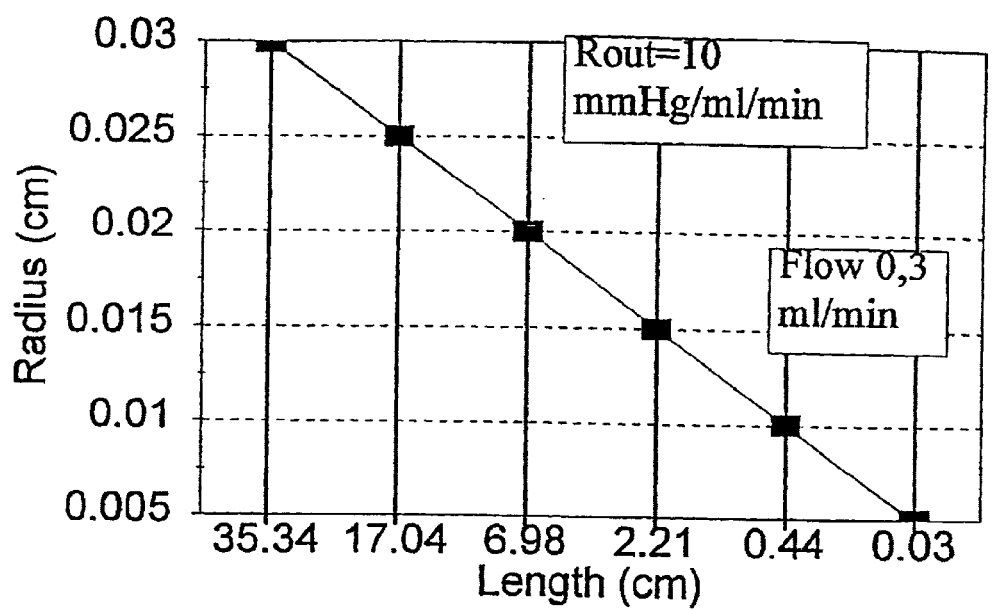
Figure 10C:
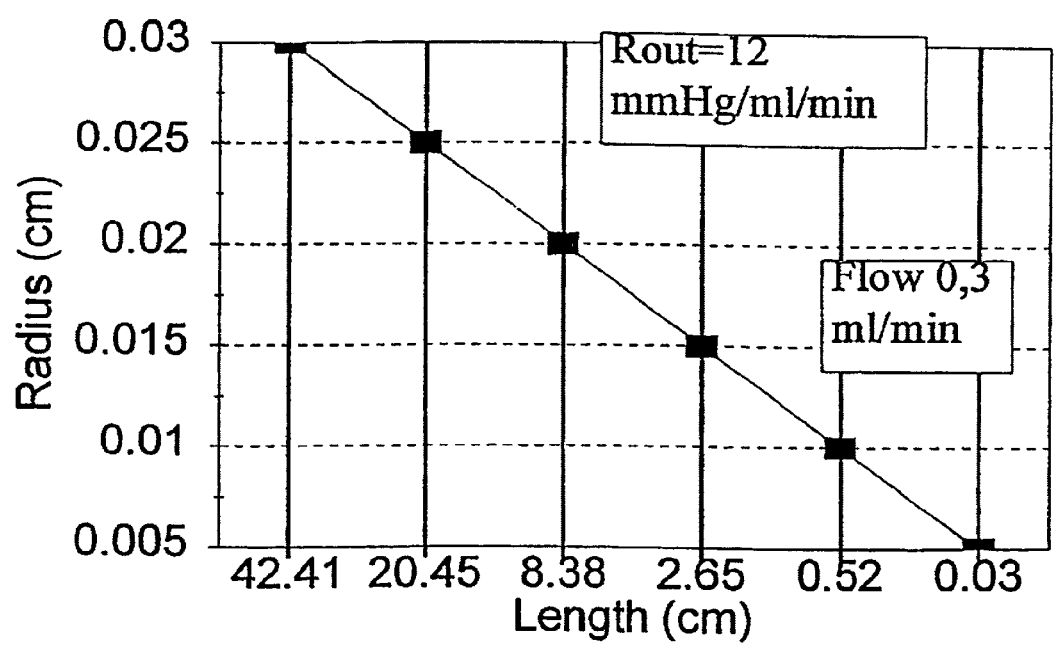

An as example, the length (L) can be calculated as follows:

$$L=((ICP-P_{ss})*\pi*R^4)/8*F*V \text{ Hagen-Poiseulle's law}$$

wherein ICP is the intracranial pressure, $P_{ss}$ is the pressure in the sagittal sinus, F is the flow rate of the cerebrospinal fluid and V is the viscosity of the cerebrospinal fluid. If $ICP-P_{ss}$ is set to be 4 mm Hg, R is set to be 0.15 mm, F is set to be 0.3 ml/min and V is set to be 0.0072 dyn*s/cm$^2$, then for a Rout between 8 and 12 mm Hg/ml/min, the length is calculated to be between 1.77 cm and 2.65 cm. In a similar manner, the dimensions of various tubular flow passage restricting means can be calculated. It will be evident that various combinations of dimensions as illustrated in FIG. 10 are within the scope of the invention.

In the laboratories of Danish Technological Institute (DTI) the dimensioning has been tested in a test bench. The results of the tests correspond to the calculated results for various dimensions. This means that it is possible to construct a shunt system that has the same resistance to outflow of CSF as the normal, "natural" CSF pathways possess. It should be noted that although the above formula can be used as a guidance, the results of the practical investigations have shown that the relationship between the resistance to outflow of CSF (Rout) and the length of the tubular flow passage restricting means is not completely linear. For practical purposes, however, Hagen-Poiseulle's law can be used to calculate appropriate dimensions of the tubular flow passage restricting means.

Figure 2:
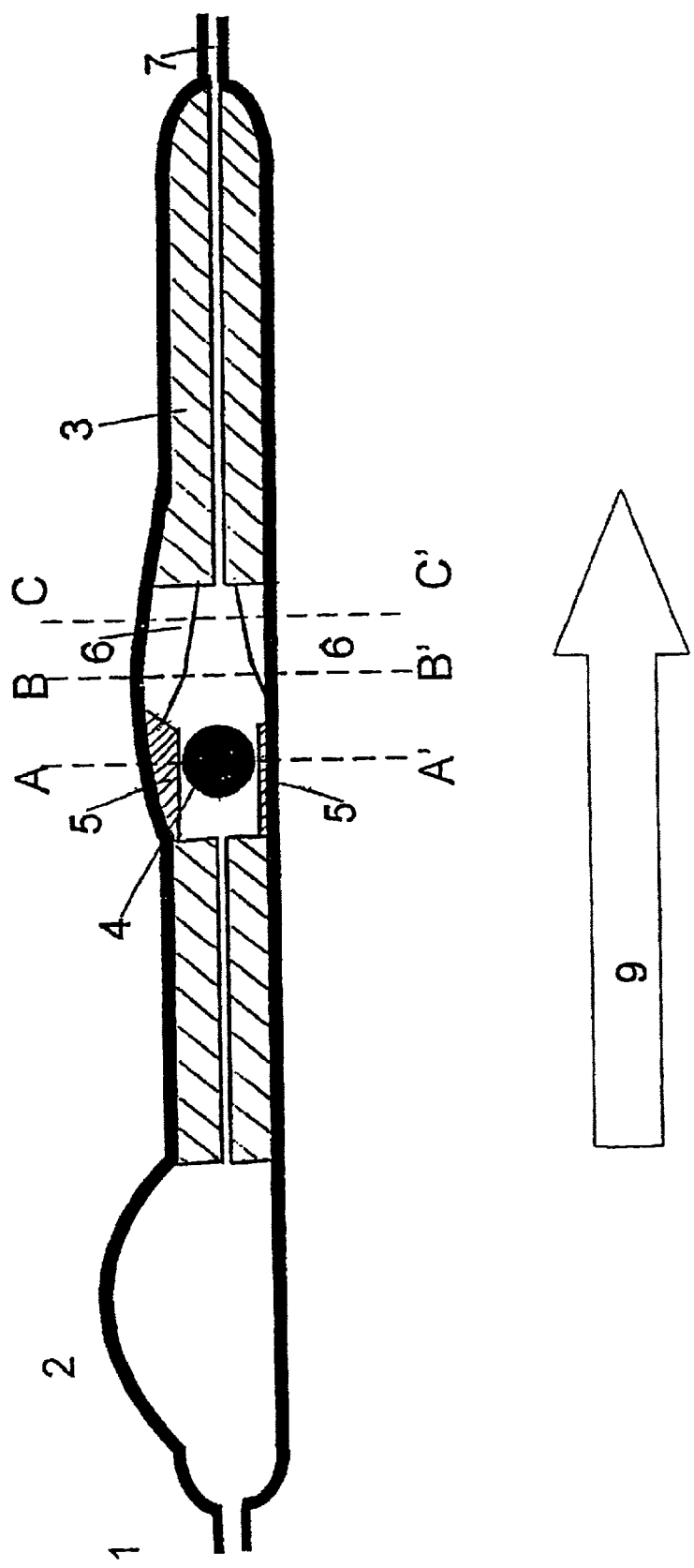
FIG. 2 is a side view of a cerebrospinal fluid shunt according to a preferred embodiment in which the flow regulator means is divided in two parts with the check valve inbetween them.
Figure 3:
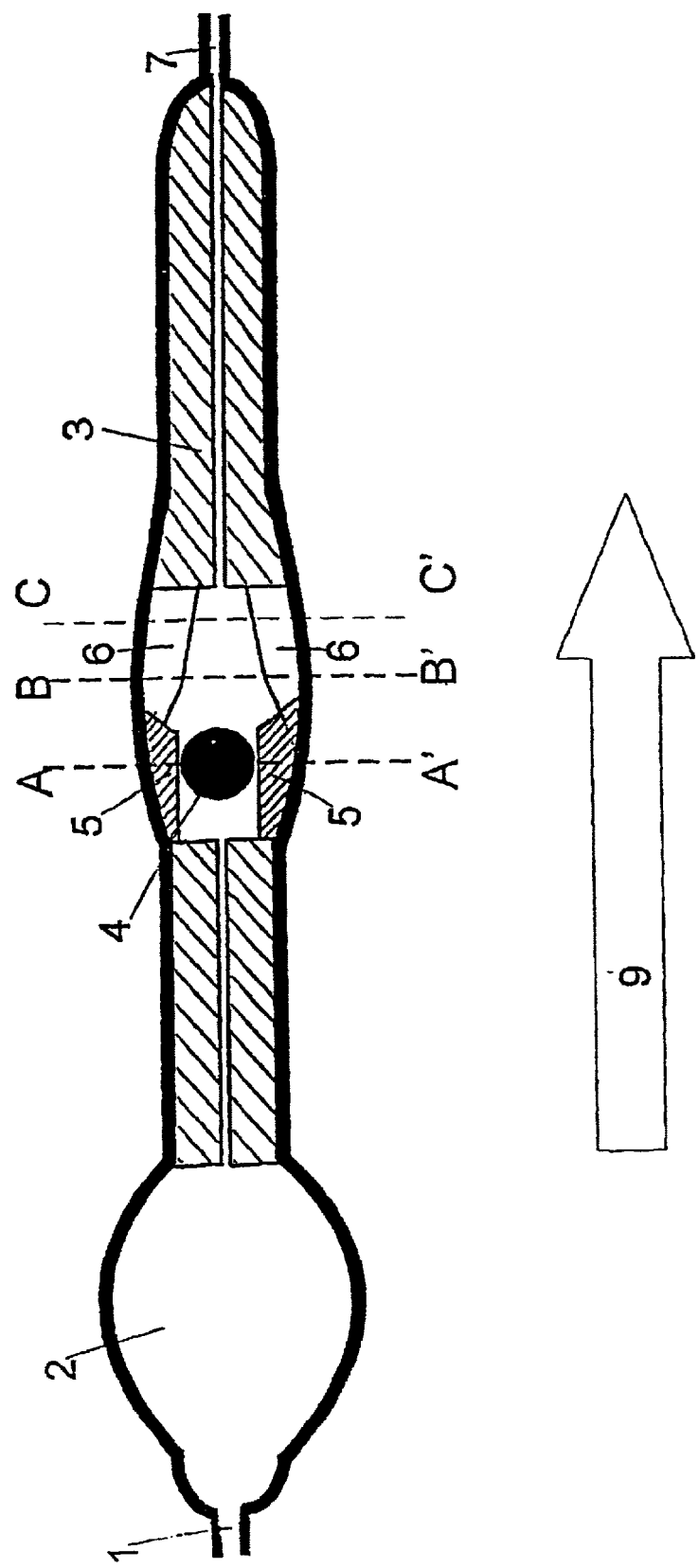
FIG. 3 is a top view of the same cerebrospinal fluid shunt.

In general, the tubular flow passage restricting means will have a length within the range of 3.5 mm to 83.8 mm, preferably within the range of 17.7 mm to 26.5 mm, such as about 22.1 mm, either in itself or defined within said shunt main body. This length may be divided in two or more individual segments, if considered appropriate, as illustrated in FIGS. 2 and 3.

BEST MODE FOR CARRYING OUT THE INVENTION

In a presently preferred embodiment, the shunt consists of a catheter for the ventricle, a body (FIGS. 1 to 6) containing the resistance device and a ball valve substantially without any inherited resistance compared to the resistance in the flow passage restricting means, and a drain to be introduced into the sagittal sinus.

Figure 8:
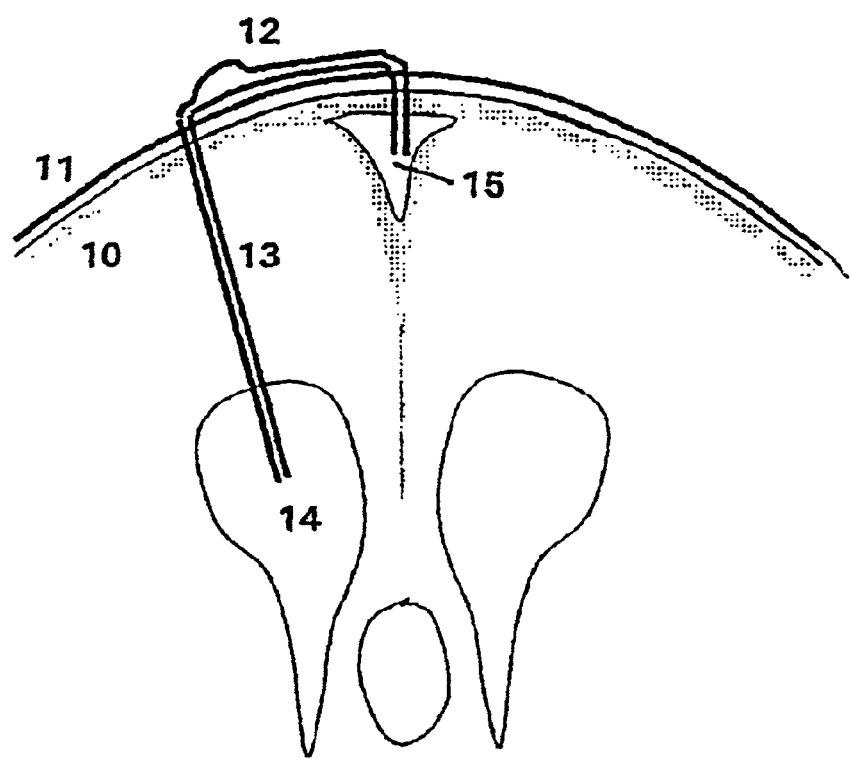
FIG. 8 is a frontal section through sinus sagittalis superior.
Figure 9:
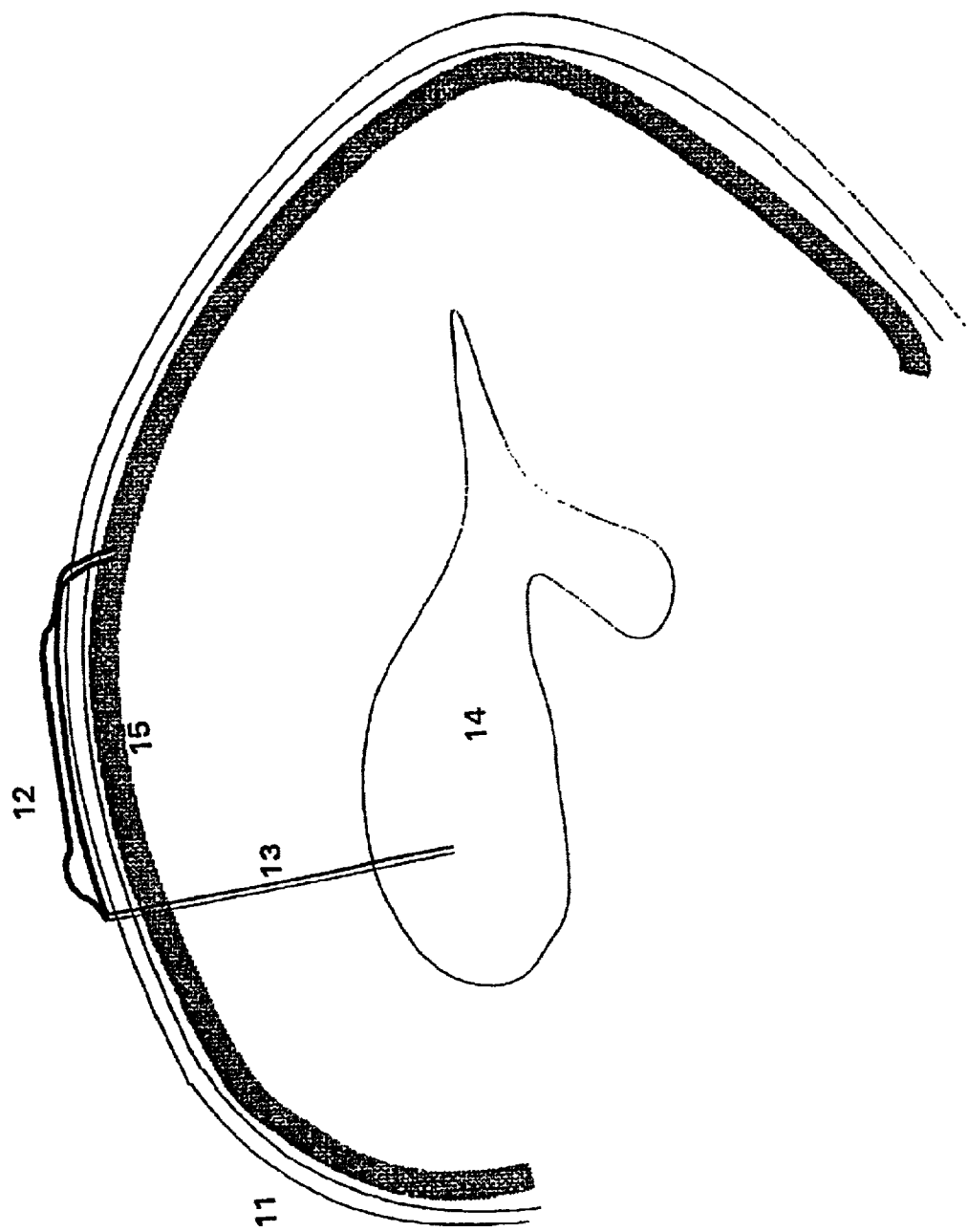
FIG. 9 is a sagittal section through sinus sagittalis.

The shunt is placed subcutaneously on the top of the calvarium, behind the coronal suture on the right (or left) side of the sagittal suture. Via a borehole a catheter is inserted in the right (or left) ventricle and connected to the body of the shunt. A small borehole (2–3 mm) is placed directly over the sagittal sinus, running in the midline beneath the readily identifiable sagittal suture. A drain of the same outer diameter as the borehole is introduced into the sagittal sinus and connected to the "distal" end of the shunt. FIGS. 8 and 9 show the principles of the location of the shunt device.

Suitable ventricular drains are well-known within the art and can e.g. be a plain, 3 mm outer diameter silicone rubber drain. Standard produced drains may be preferred.

In a presently preferred embodiment, the shunt main body is constructed from a suitable material such as a silicone rubber and has preferably an antechamber with a perforable dome. In the proximal ("the top") end the dome ends in a tip where the ventricular drain can be connected and secured. In the distal end of the dome the inlet to the flow regulator is placed.

The antechamber will generally have a flat bottom consisting of hard silicone rubber. The dome is made of soft, perforable, self-healing silicone rubber. The ventricular drain is attached to the inlet connector, which is provided with a brim. The length of the connector is generally about 5 mm. The drain is secured the usual way e.g. by a ligature. The antechamber is attached to the tubule containing the tubular flow passage restricting means.

The tubular flow passage restricting means is dimensioned according to Hagen-Poiseulle's law to a resistance to flow at about 8–12 mm Hg/ml/min such as 10 mm Hg/ml/min. In a presently preferred embodiment the tubular flow passage restricting means has a length of about 22.1 mm which may be divided into two parts (see FIGS. 2 and 3) and the internal radius of the flow-restricting part of the device is 0.15 mm. The tubular flow passage restricting means is substantially straight and the walls are substantially smooth. The material of the tubular flow passage restricting means can be hard silicone rubber or HD polyethylene (e.g. gas sterilized polypropylene), polycarbonate, polysulfone, polystyrene or PVC. Alternatively, the tube can be of titanium.

The valve means may consist of a chamber into which the flow regulating tube ends in a bowl (FIGS. 1–3 and 5–7). A ball made of a material with the same mass weight as CSF is placed in the chamber. Examples of such material are polyethylene, polysulfone, polystyrene and glass with air inside. The distal end of the chamber leads to the tubule where the drain for the sagittal sinus is to be attached. In one embodiment, three ridges stop the ball from occluding the flow in the direction of the sagittal sinus. FIGS. 2–4 show an alternative embodiment wherein the housing is circular or oval and designed so that the ball is only supported by two ridges at a time, said ridges having sharp contours in order to avoid "adhesion".

Figure 5:
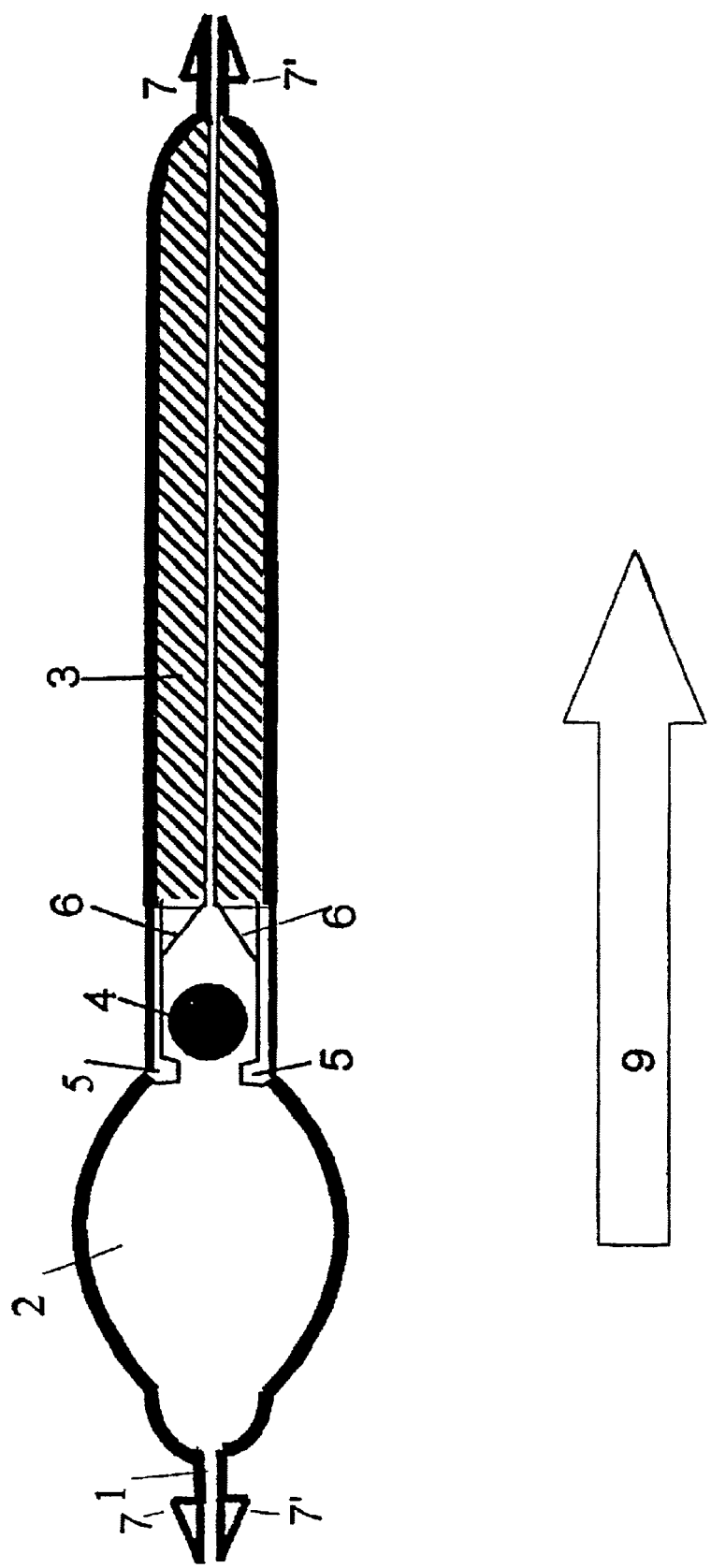
FIG. 5 shows the cerebrospinal fluid shunt with an antechamber, a unidirectional check valve and a flow regulating tube, top view.
Figure 6:
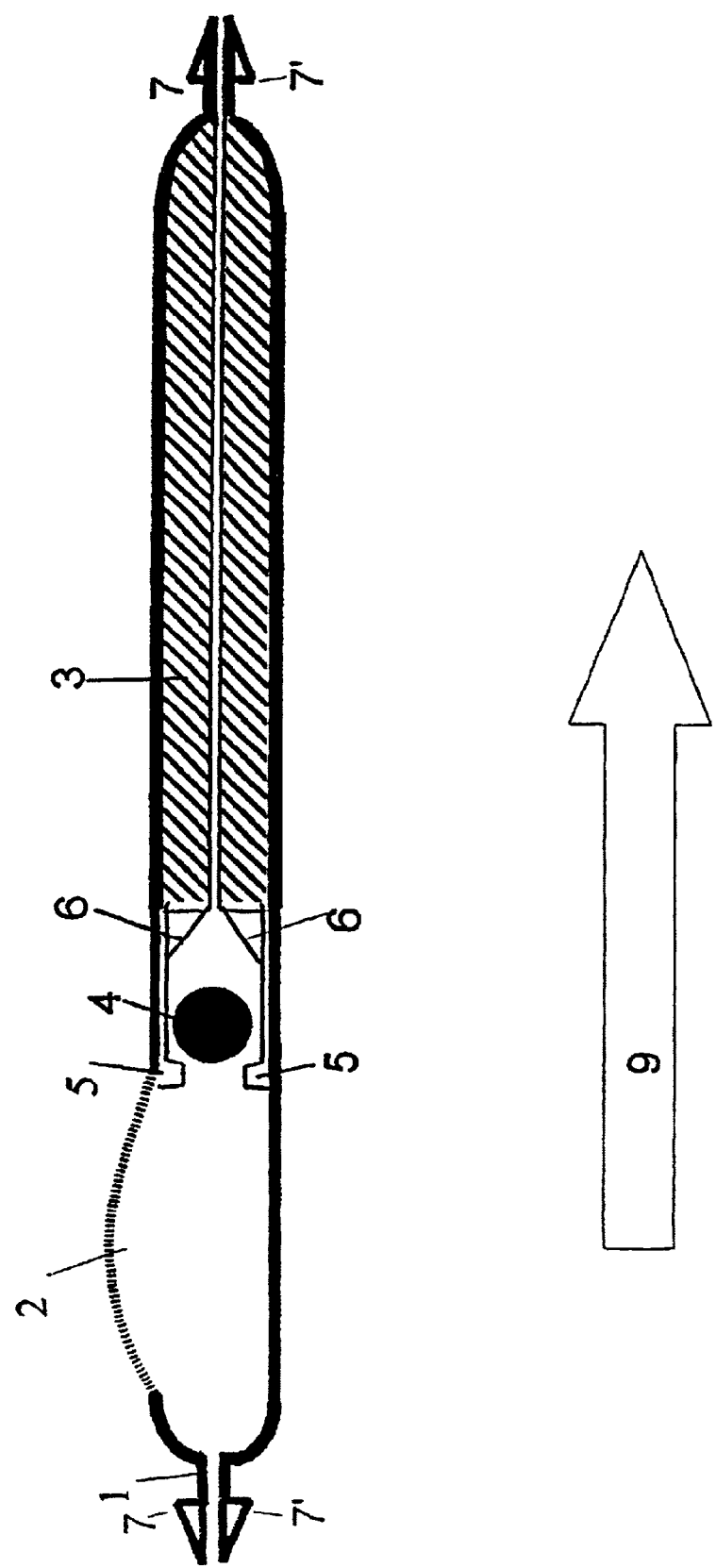
FIG. 6 shows the cerebrospinal fluid shunt in a lateral view.
Figure 7:
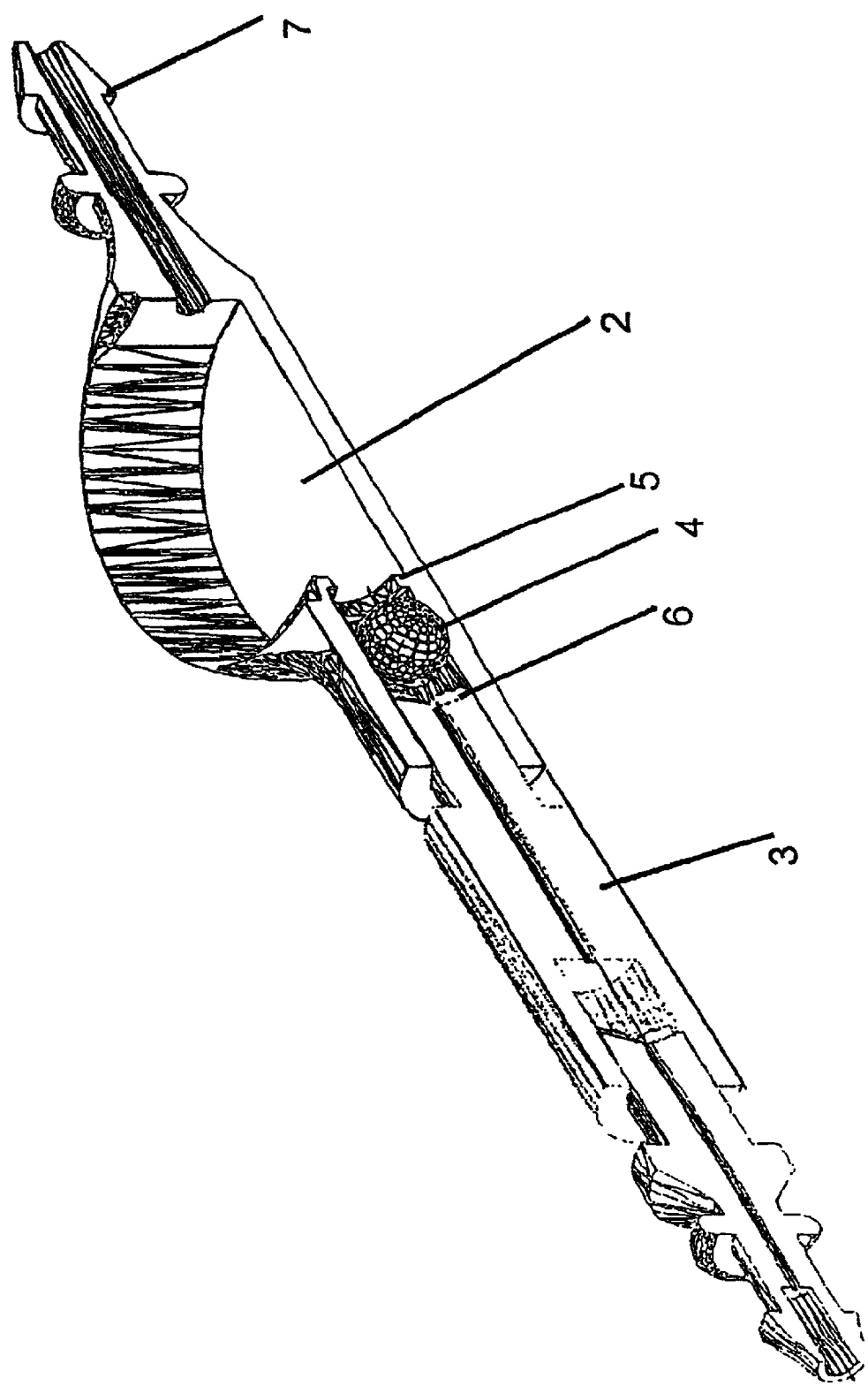
FIG. 7 shows the cerebrospinal fluid shunt in a three-dimensional view.

Alternatively, the check valve could be placed at the inlet end of the flow regulating tube. As an example, the valve means may consist of said ball embodied in a chamber ending at the inlet end of the tube in sharp ridges. The opening into the antechamber may be circular, the edges of the hole rigid, and the diameter of the hole smaller than the ball (FIGS. 5–7).

The valve mechanism may be constructed with a flat back side (see FIG. 2). The outlet of the first flow-regulating tube may be provided with soft lips or have an excavation matching the periphery of the ball.

Alternatively, the check valve means could be with guided rigid valve members, e.g. shaped as rings, or be with flexible valve members e.g. with tongue-shaped laminae.

The drain for the sagittal sinus may be made of e.g. titanium tube or silicone rubber tube. The distal 5 mm of the tube will generally have an outer diameter of 2 mm and an inner diameter of 1.5 mm. The part of the drain that goes through the skull has generally an outer diameter of 3 mm, the inner diameter is 1.5 mm. The part of the drain with the largest diameter may be shortened to fit the distance from the body of the shunt to the hole over the sagittal sinus.

Another design of the drain is to use a titanium tube with an inner diameter of 1.5 mm and a length of 20 mm. The tube is attached to a silicone rubber tube with outer/inner diameter 3/1.5 mm and of 60 mm length. The titanium tube is readily inserted via a 2 mm wide borehole through the bone covering the sagittal sinus. A stilet in the tube allows the inserted tube to be angled somewhat to lead the silicone rubber tube following the surface of the skull to the body of the shunt.

References

EP 066 685
U.S. Pat. No. 4,605,395
U.S. Pat. No. 4,781,673
U.S. Pat. No. 4,904,236
Aschoff A, Kremer P, Benesch C, Fruh K, Klank A, Kunze S. overdrainage and shunt technology. A critical comparison of programmable, hydrostatic and variable-resistance valves and flow-reducing devices. Child's Nerv. Syst. 1995; 11:193–202
Borgesen S E, Gjerris F. The predictive value of conductance to outflow of CSF in normal hydrocephalus. Brain 1982; 105:65–86
Borgesen S E, Gjerris F. The relationships between intracranial pressure, ventricular size and resistance to CSF outflow. J Neurosurg 1987;67:535–39
Borgesen S E, Gjerris F, Schmidt J. Measurement of resistance to CSF outflow by subarachnoid perfusion. In:
Gjerris F, Borgesen S E, Sorensen P S, eds. Outflow of cerebrospinal fluid. Copenhagen: Munksgaard, 1989, pp 12–29.
Borgesen S E, Gjerris F, Fedderss O, et al.: Measurement of resistance to outflow. Clinical experiences in 333 patients. In Hoff I, Betz A L (eds.): Intracranial pressure VII, Berlin, Springer Verlag: 353–355, 1987.
Drake J M, Sainte-Rose C The Shunt Book, pp 146, Blackwell Science 1995.
Hash C J, Shenkin H A, Crowder L E Ventricle to sagittal sinus shunt for hydrocephalus. Neurosurgery 1979;4: 394–400.
Wen H L Ventriculo-superior sagittal sinus shunt for hydrocephalus. Surg. Neurol. 1981; 17: 432-434.

Legends to Figures of Flow Regulator and Valve Mechanism
1. Connector tube for ventricular drain.
2. Antechamber, compressible and perforable dome.
3. Flow regulating tubes, dimensioned to a constant resistance to flow, may be divided in two parts by a valve mechanism.
4. Ball, polyethylene, mass weight equal to cerebrospinal fluid.
5. Ridges controlling movement of ball, distance between the edges equals diameter of ball. Ball is pressed upstream when flow is inverted and prevents flow when pressed against the outlet of the tube.
6. Ridges controlling movement of ball at distal (downstream) end of valve. Ridges narrowing to a lesser diameter than ball, stopping the ball from closing the inlet of the second part of the flow regulator when flow is from ventricles to sagittal sinus.
7. Connector tube for sagittal sinus drain.
7'. Collar of connector tube.
8. Check valve.
9. Direction of flow.
10. Dura mater.
11. The skull.
12. Shunt main body.
13. Ventricle catheter.
14. Ventricle.
15. Sinus sagittalis.

What is claimed is:

1. A cerebrospinal fluid shunt system comprising:
    brain ventricle catheter to insert into the brain ventricle so to drain cerebrospinal fluid from the brain ventricle;
    sinus sagittalis catheter to insert into the sinus sagittalis for feeding the cerebrospinal fluid into the sinus sagittalis;
    shunt main body connected at one location thereof to the brain ventricle catheter and at another location thereof to the sinus sagittalis catheter to provide fluidic communication between the brain ventricle catheter and the sinus sagittalis catheter, and
    flow restricting passage defined within the shunt main body to maintain a substantially constant resistance to flow of the shunt system within the range of 8–12 mmHg/ml/min.

2. A cerebrospinal fluid shunt system according to claim 1, wherein the substantially constant resistance to flow of the shunt system is about 10 mmHg/ml/min.

3. A cerebrospinal fluid shunt system according to claim 1, further comprising a check valve within the shunt main body to prevent the cerebrospinal fluid from flowing back from the sinus sagittalis catheter to the brain ventricle catheter.

4. A cerebrospinal fluid shunt system according to claim 1, wherein the flow restricting passage comprises a tubular passage having an internal radius of about 0.20 mm or less.

5. A cerebrospinal fluid shunt system comprising:
    a brain ventricle catheter sized to insert into a brain ventricle of a person so as to drain cerebrospinal fluid from the brain ventricle;
    a sinus sagittalis catheter sized to insert into a sinus sagittalis of a person to feed cerebrospinal fluid into the sinus sagittalis;
    a main body connected at one location thereon to the brain ventricle catheter and at another location thereon to the sinus sagittalis catheter to provide fluidic communication between the brain ventricle catheter and the sinus sagittalis catheter; and a flow restricting passage structure defined within the main body to maintain a substantially constant resistance to flow of the shunt system within the range of 8–12 mmHg/ml/min independent of an orientation of the main body.

6. A cerebrospinal fluid shunt system according to claim 1, wherein the flow restricting passage maintains the substantially constant resistance to flow independent of an orientation of the shunt main body.

7. A cerebrospinal fluid shunt system according to claim 1, wherein the substantially constant resistance to flow of the shunt system is about 10 mmHg/ml/min.

8. A cerebrospinal fluid shunt system according to claim 1, wherein the substantially constant resistance to flow of the shunt system is about 8 mmHg/ml/min.

9. A cerebrospinal fluid shunt system according to claim 5, wherein the flow restricting passage comprises a tubular passage having an internal radius of about 0.20 mm or less.

10. A cerebrospinal fluid shunt system according to claim 5, wherein the brain ventricle catheter is connected to a first end of the main body, and the sinus sagittalis catheter is connected to a second end of the main body.

11. A cerebrospinal fluid shunt system comprising:
  means for insertion into the brain ventricle so as to drain cerebrospinal fluid from the brain ventricle;
  means for insertion into the sinus sagittalis for feeding the cerebrospinal fluid into the sinus sagittalis;
  means for providing fluidic communication between the means for insertion into the brain ventricle and the means for insertion into the sinus sagittalis, the means for providing fluidic communication connected at one location thereof to the means for insertion into the brain ventricle and at another locations thereof to the means for insertion into the sinus sagittalis; and
  means, defined within the means for providing fluidic communication, for maintaining a substantially constant resistance to flow of the shunt system within the range of 8–12 mmHg/ml/min.

12. A cerebrospinal fluid shunt system according to claim 11, wherein the substantially constant resistance to flow of the shunt system is about 10 mmHg/ml/min.

13. A cerebrospinal fluid shunt system according to claim 11, further comprising means, disposed within the means for providing fluidic communication, for preventing the cerebrospinal fluid from flowing back from the means for insertion into the sinus sagittalis to the means for insertion into the brain ventricle.

14. A cerebrospinal fluid shunt system according to claim 11, wherein the means for maintaining a resistance to flow comprises a tubular passage having an internal radius of about 0.20 mm or less.

15. A cerebrospinal fluid shunt system according to claim 11, wherein the means for maintaining a substantially constant resistance to flow maintains a resistance to flow of the shunt system of 8–12 mmHg/ml/min, independent of an orientation of the means for providing fluidic communication.

16. A cerebrospinal fluid shunt system comprising:
  a shunt body sized to extend between a brain ventricle of a person and a sinus sagittalis of the person to provide fluidic communication between the brain ventricle and the sinus sagittalis, the shunt body having a flow restricting structure defined therein to maintain a substantially constant resistance to flow of the shunt system within the range of 8–12 mmHg/ml/min independent of an orientation of the shunt body.

17. A cerebrospinal fluid shunt system according to claim 16, wherein the substantially constant resistance to flow of the shunt system is about 8 mmHg/ml/min.

18. A cerebrospinal fluid shunt system according to claim 16 wherein the substantially constant resistance to flow of the shunt system is about 0.12 mmHg/ml/min.

19. A cerebrospinal fluid shunt system according to claim 1, wherein the substantially constant resistance to flow of the shunt system is about 8 mmHg/ml/min.

20. A cerebrospinal fluid shunt system according to claim 1, wherein the substantially constant flow of the shunt system is about 10 mmHg/ml/min.

21. A cerebrospinal fluid shunt system according to claim 5, wherein the substantially constant resistance to flow of the shunt system is about 8 mmHg/ml/min.

22. A cerebrospinal fluid shunt system according to claim 5, wherein the substantially constant resistance to flow of the shunt system is about 12 mmHg/ml/min.

23. A cerebrospinal fluid shunt system according to claim 11, wherein the substantially constant resistance to flow of the shunt system is about 8 mmHg/ml/min.

24. A cerebrospinal fluid shunt system according to claim 11, wherein the substantially constant resistance to flow of the shunt system is about 12 mmHg/ml/min.

25. A cerebrospinal fluid shunt system according to claim 1, wherein the flow restricting passage comprises a tubular passage having an internal radius of about 0.15 mm.

26. A cerebrospinal fluid shunt system according to claim 1, wherein the flow restricting passage comprises a tubular passage having an internal radius of about 0.10 mm.

27. A cerebrospinal fluid shunt system according to claim 5, wherein the flow restricting passage comprises a tubular passage having an internal radius of about 0.15 mm.

28. A cerebrospinal fluid shunt system according to claim 5, wherein the flow restricting passage comprises a tubular passage having an internal radius of about 0.10 mm.

29. A cerebrospinal fluid shunt system according to claim 11, wherein the flow restricting passage comprises a tubular passage having an internal radius of about 0.15 mm.

30. A cerebrospinal fluid system according to claim 11, wherein the flow restricting passage comprises a tubular passage having an internal radius of about 0.10 mm.

31. A cerebrospinal fluid shunt system in situ, comprising:
  a brain ventricle catheter having an end thereof inserted into a brain ventricle of a patient, so as to drain cerebrospinal fluid from the brain ventricle;
  a sinus sagittalis catheter having an end thereof inserted into the sinus sagittalis of the patient for feeding of the cerebrospinal fluid from the brain ventricle into the sinus sagittalis;
  a shunt main body connected at one location thereof to the brain ventricle catheter and at another location thereof to the sinus sagittalis catheter to provide fluidic communication between the brain ventricle catheter and the sinus sagittalis catheter; and
  a flow restricting passage defined within the shunt main body to maintain a substantially constant resistance to flow from the brain ventricle to the sinus sagittalis within the range of 8–12 mmHg/ml/min.

* * * * *